United States Patent [19]

LeVeen et al.

[11] 4,404,971

[45] Sep. 20, 1983

[54] DUAL BALLOON CATHETER

[76] Inventors: Harry H. LeVeen, 321 Confederate Cir., Charleston, S.C. 29407; Eric G. LeVeen, 3-3 Woodlike Rd., Albany, N.Y. 12203; Robert F. LeVeen, 312 Lombard St., Philadelphia, Pa. 19147

[21] Appl. No.: 250,603

[22] Filed: Apr. 3, 1981

[51] Int. Cl.³ ............................................. A61M 25/00
[52] U.S. Cl. ................................. 128/348.1; 604/101; 604/53; 128/325
[58] Field of Search ............ 128/325, 344, 348–350 R, 128/214.4, 348.1; 604/49–53, 101

[56] References Cited

U.S. PATENT DOCUMENTS 3,411,506 11/1968 Velasco ........................... 128/349 B
3,833,003 9/1974 Taricco ............................... 128/347
3,991,767 11/1976 Miller et al. ........................ 128/348
4,323,071 4/1982 Simpson et al. ............ 128/349 B X

FOREIGN PATENT DOCUMENTS 1069823 11/1959 Fed. Rep. of Germany ...... 128/344

Primary Examiner—Dalton L. Truluck
Attorney, Agent, or Firm—Brooks, Haidt, Haffner & Delahunty

[57] ABSTRACT

A technique and a device for cutting off the flow of blood through an unwanted opening in a major blood vessel to facilitate surgical closure of the opening utilizing a dual balloon catheter inserted into the blood vessel with the balloons inflated on opposite sides of the opening.

1 Claim, 4 Drawing Figures

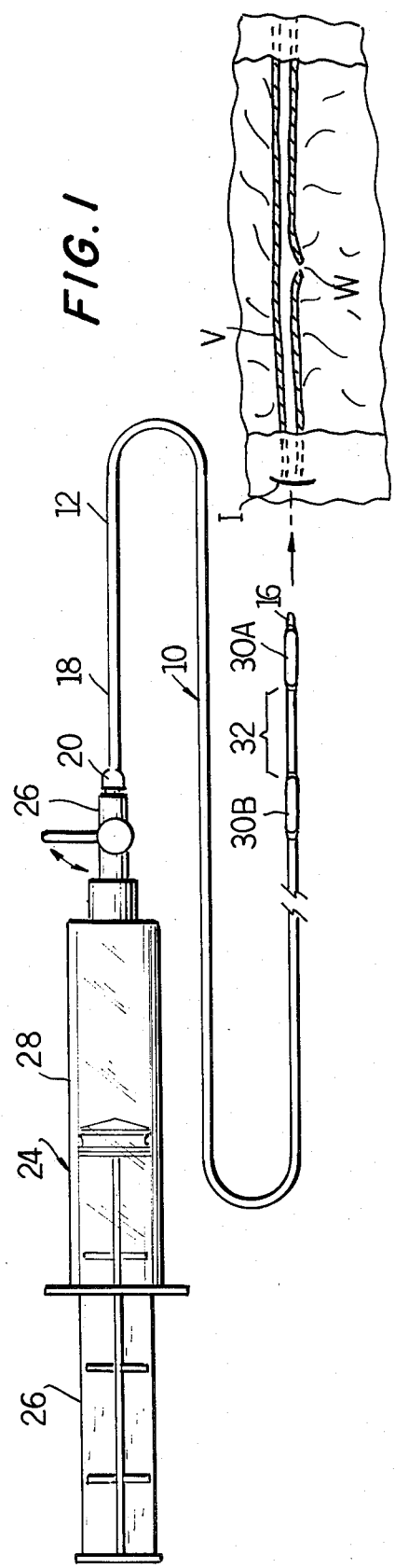
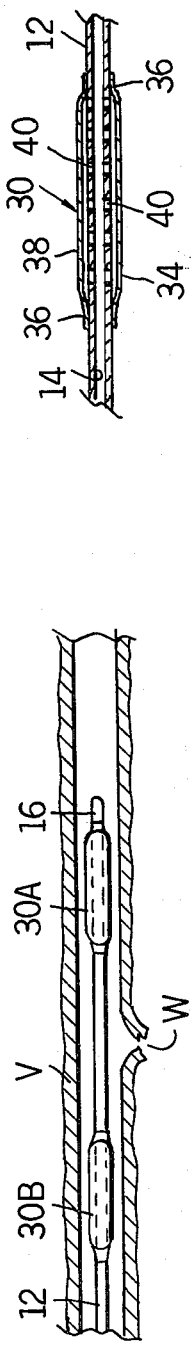
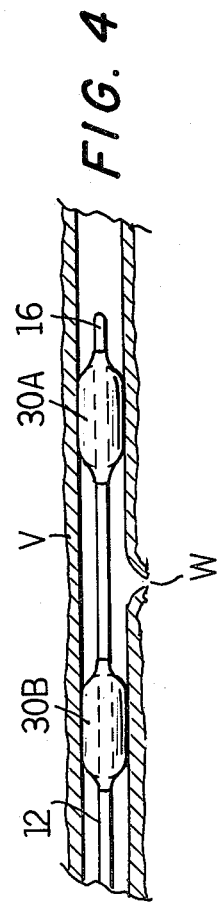
FIG. 1
FIG. 2
FIG. 3
FIG. 4

DUAL BALLOON CATHETER

This invention relates to vascular surgery and in particular provides a technique and device having particular utility for closing rapidly bleeding wounds in blood vessels in which the flow of blood from the wound, or in which the location of the blood vessel prevents visual inspection of the damage and consequently impedes its repair.

In surgery, such as in the surgical removal of tumors located in the body near major blood vessels, there is an ever present danger that a major blood vessel may be inadvertently entered resulting in a wound with a rapid flow of blood. When the blood vessel is so located that the wound is obscured, or when the flow of blood is itself so rapid as to obscure the wound, thus impeding repair, the patient may expire from blood loss before the wound can be closed.

It is thus a principal object of this invention to provide a technique and a device which can be utilized to cut off the flow of blood through an inadvertent opening in a major blood vessel to facilitate surgical closure of the opening.

This and other objects of the invention are essentially obtained utilizing a catheter having a pair of inflatable balloons located adjacent an end of the catheter. In accordance with this invention the balloons can be inflated by introducing a fluid under pressure into the interior of the catheter through the other end of the catheter which is connected to a suitable device for so introducing such a fluid, for example, a syringe. The catheter should further be provided at its end connected to the fluid pressuring device with some means of retaining fluid pressure on the catheter.

In accordance with the invention the end of the catheter with the balloons deflated is introduced into a blood vessel which is rapidly accessible by minor surgery and which communicates with the blood vessel to be repaired. The end of the catheter with the deflated balloons is then advanced into the blood vessel to be repaired and positioned such that the two balloon forming devices are located on opposite sides of the opening to be repaired. Fluid is then introduced into the catheter and pressured to expand the balloons to a point that these close the blood vessel on each side of the wound preventing flow of blood through the vessel at that location. Surgical repair of the opening is then made while the pressure is continued on the balloons. After the surgical repair has been completed the balloons are deflated by releasing pressure on the fluid, and the catheter is removed.

For a more complete understanding of the practical application of this invention reference is made to the appended drawings in which:

FIG. 1 is an elevational view of a catheter in accordance with the present invention including a pressuring device and illustrating somewhat diagramatically and partially in section a point of entry into a blood vessel having a wound which is to be repaired;

FIG. 2 is a fragmentary section of the catheter shown in FIG. 1;

FIG. 3 is a view showing a portion of the catheter at its positioning point in a blood vessel; and FIG. 4 is a view similar to FIG. 3 showing the balloons of the catheter inflated.

Referring more particularly to FIG. 1 the reference numeral 10 generally indicates a dual balloon catheter in accordance with the present invention. Catheter 10 includes an elongated tube 12 constructed of polyurethane or similar inert material having central bore 14 (see FIG. 2) extending throughout its length. At one end 16 of catheter 10 bore 14 of tube 12 is closed. At the other end 18 a male luer fitting 20 is provided which communicates interiorally with bore 14 and which is received in corresponding female fitting of a one-way valve 22 mounted on a syringe 24. Valve 22 has a position closing off communication to bore 14 and a second position communicating bore 14 with the interior of syringe 24 such that by forcing the plunger 26 of syringe 24 into its barrel 28 fluid (normally air) contained within barrel 28 is forced into bore 14.

Catheter 10 is provided with two balloon forming structures 30, one of which is shown in section in FIG. 2. For convenience, in the other figures, one balloon forming structure is designated as 30A and is located adjacent closed end 16 of catheter 10. The other balloon forming structure is designated in those other figures as 30B and is located away from end 16 spaced apart from balloon forming structure 30A by a short distance along the length of tube 12 indicated by the reference numeral 32 in FIG. 1.

Referring more particularly to FIG. 2, each balloon forming structure 30 includes a more or less cylindrical wall in the form of a sleeve 34 snugly overlying and extended about tube 12. Sleeve 34 is formed of rubber or other inert elastomeric material and is sufficiently thin that it is freely extendible with little force. Sleeve 34 is secured to tube 12 at its ends, with a fluid tight seal formed by wrapping the ends with a serving of silk thread indicated by the reference numeral 36. Thus an annular space 38 is trapped between the exterior of tube 12 and the interior of sleeve 34. A series of ports 40 through tube 12 communicate the interior of bore 14 with annular space 38.

In FIG. 1 the reference letter V indicates in section a blood vessel which during surgery has inadvertently been entered forming a wound W. An incision I is made in a blood vessel communicating with blood vessel V, and closed end 16 of catheter 12 is inserted into incision I and introduced into blood vessel V as shown in FIG. 3 to a position at which balloon forming structures 30A and 30B are on opposite sides of wound W. The location of catheter 10 in vessel V can be felt to determine precise location. Stopcock 22 is then positioned such that communication between bore 14 and the interior of barrel 28 is open. Plunger 26 is then introduced into barrel 28 to a position in which balloons 30A and 30B are inflated to bring them into contact with the walls of blood vessel V, as shown in FIG. 4. Stopcock 22 is then moved to the closed position. Wound 12 is sutured. Then stopcock 22 is again moved to open position, and plunger 26 is withdrawn from barrel 28 deflating balloon forming structures 30A and 30B. Catheter 10 is withdrawn, and incision I closed.

Example I

The patient had a carcinoma of the head of the pancreas. In dissecting the pancreas from the portal vein, which is covered by the pancreas, the portal vein was inadvertently entered in an area which was infiltrated by cancer. Rapid bleeding ensued. The bleeding site was totally inaccessible since the pancreas obscured visibility. Before the area could have been exposed and the portal vein sutured, the patient would have expired. A segment of the small bowel was elevated to expose its mesentery. A small vein in the mesentery was opened, and a deflated dual balloon catheter was inserted into the vein, closed end first, and extended up to a position in the portal vein where it could be felt and positioned by touch such that the two balloon forming structures were on opposite sides of the point of entry to be repaired. The balloons were inflated, and bleeding immediately ceased. It was then possible to expose the portal vein and suture the hole.

A suitable catheter in accordance with this invention can be constructed utilizing a flexible extruded tubing of polyurethane of a diameter of 5 french. The catheter should have a length of approximately 85 centimeters and an outside diameter of between 2 mm and 6 mm. The interior volume of the balloons will depend on the size of the vessel to be obturated. The device has two small rubber sleeves over side holes which communicate with the central lumen of the tubing. The sleeves have a length of approximately 1.5 cm.

A series of pin hole openings had theretofore been made in the catheter beneath the location of the sleeves. Both sleeves are internally ported through the wall of the catheter to its interior. When the pressure in bore 14 is raised to approximately 2 atmospheres, each of sleeves 30 is expanded by filling the air space in annular space 38 to approximately a diameter of 11 millimeters when unimpeded. The device as described is useful in occluding blood flow through blood vessels having diameter on the order of 6-10 millimeters.

It will be noted that all the preceding description was of a catheter 10 having a single bore 14 communicating with both balloon forming devices 30A and 30B. In certain circumstances it may be desirable to divide the bore 14 into two separate interior tubes one leading to each of the balloon forming devices 30A and 30B, respectively, and to provide for pressuring each such tube separately. It is even feasible, where desired, to introduce a third tubing leading down the bore of the catheter communicating through the wall of tube 12 between the locations of the two balloon forming devices to permit introduction of fluid or removal of fluid at the location of the wound. These and other variations readily suggest themselves within the scope of this invention.

While the most usual use of the double balloon catheter will be to arrest hemmorrhage from an unwanted opening into a major vessel at the time of surgery, the double balloon catheter can be used to arrest bleeding from rupture of the vessel wall due to a weakness such as an aneurysm. In ruptured abdominal aortic aneurysms, which occur not infrequently in elderly patients, the patient often bleeds to death before the bleeding can be surgically controlled. With the present invention, the catheter can be introduced through the femoral artery quickly and pushed upward through the aneurysm. With balloons placed on either side of the aneurysm bleeding is controlled until the proper surgical exposure and clamping can be accomplished.

Major injuries can also lead to arterial rupture and death from bleeding. The double balloon catheter in such cases would serve to control the bleeding until the proper repair can be performed.

We claim:

1. A method of closing an opening in a first blood vessel which comprises introducing the closed end of a catheter into a second blood vessel remote from and communicating with said first blood vessel; the said catheter being formed of an elongated tube having a central bore extending the length thereof, said bore being closed at one end of said catheter and having means for introducing a pressurized fluid into said bore at the other end of said catheter, said catheter further including first balloon forming structure disposed about said tube adjacent the closed end of said catheter, second balloon forming structure disposed about said tube spaced along the length thereof apart from said first balloon forming structure, each said balloon forming structure having an expandable cylindrical wall enclosing said tube and sealed at the ends thereof to said tube thereby trapping an annular closed space between said wall and said tube, and first and second ports in said tube communicating the interior bore thereof with said closed spaces trapped by said walls of said first and said second balloon forming structures, respectively; advancing said catheter in said blood vessels to a position in said first blood vessel with said first and second balloon forming structures disposed on opposite sides of said opening; introducing fluid under pressure into said catheter through said means at the other end of said catheter thereby causing said fluid to flow into said closed spaces and expanding said walls to an oblate shape blocking flow of blood in said first blood vessel; surgically closing said opening while retaining pressure on said fluid; removing pressure from said fluid after closing said opening thereby to deflate said balloon forming structures; and removing said catheter from said blood vessels.

* * * * *